(12) United States Patent
Tang et al.

(10) Patent No.: US 8,450,100 B2
(45) Date of Patent: May 28, 2013

(54) **COLLAGEN PEPTIDE HAVING IMMUNE-ENHANCING ACTIVITY FROM *CYANEA NOZAKII* AND PREPARATION METHOD AND USES THEREOF**

(75) Inventors: Luhong Tang, Wuxi (CN); Bentian Zhang, Wuxi (CN); Chao Deng, Wuxi (CN); Dan Lin, Wuxi (CN); Qi Wang, Wuxi (CN); Wei Chen, Wuxi (CN)

(73) Assignees: Lili Zhang, Shanghai (CN); Jiangnan University, New District, Wuxi (CN)

( * ) Notice: Subject to any disclaimer, the term of this patent is extended or adjusted under 35 U.S.C. 154(b) by 42 days.

(21) Appl. No.: 12/993,819

(22) PCT Filed: Sep. 17, 2008

(86) PCT No.: PCT/CN2008/072397
§ 371 (c)(1),
(2), (4) Date: Nov. 19, 2010

(87) PCT Pub. No.: WO2009/140833
PCT Pub. Date: Nov. 26, 2009

(65) Prior Publication Data
US 2011/0077382 A1    Mar. 31, 2011

(30) Foreign Application Priority Data
May 20, 2008    (CN) .......................... 2008 1 0024914

(51) Int. Cl.
*C07K 14/78* (2006.01)
*C07K 9/00* (2006.01)
*C12S 3/16* (2006.01)

(52) U.S. Cl.
USPC ........... 435/273; 530/356; 530/325; 530/326; 530/327

(58) Field of Classification Search
USPC ................... 435/273; 530/356, 325, 326, 327
See application file for complete search history.

(56) References Cited

FOREIGN PATENT DOCUMENTS
CN          101156643 A  *  4/2008
WO  PCT/CN2008/072397      2/2009

OTHER PUBLICATIONS
Machine translation of CN 101156643 in English.*

* cited by examiner

*Primary Examiner* — Chih-Min Kam
(74) *Attorney, Agent, or Firm* — Global IP Services; Tianhua Gu

(57) ABSTRACT

A collagen peptide with immune-enhancing activity from *Cyanea nozakii*, and a preparation method thereof are provided. The collagen peptide contains 80-90 wt % of proteins and 10-20 wt % of sugars, and has an average molecular weight of 1,000-3,000 Dalton. Monosaccharide contained in the collagen peptide are mainly glucose, glycine accounts for 16% or above and the sum of proline and hydroxyproline accounts for 18% or above of amino acids contained therein. The collagen peptide is capable of being used for preparation of medicines, health products, and skincare cosmetics having immune-enhancing function.

10 Claims, No Drawings

COLLAGEN PEPTIDE HAVING IMMUNE-ENHANCING ACTIVITY FROM *CYANEA NOZAKII* AND PREPARATION METHOD AND USES THEREOF

CROSS REFERENCE TO RELATED PATENT APPLICATION

The present application is the US national stage of PCT/CN2008/072397 filed on Sep. 17, 2008, which claims the priority of the Chinese patent application No. 200810024914.6 filed on May 20, 2008, which application is incorporated herein by reference.

BACKGROUND OF THE INVENTION

1. Field of Invention

The present invention relates to the field of natural bioactive substances, and more particularly to a collagen peptide with immune-enhancing activity from *Cyanea nozakii*, and a preparation method thereof.

2. Related Art

*Cyanea nozakii* is a large marine plankton commonly known as jellyfish, and belongs to Family Cyanea, Order Phylum cnidaria, Class Scyphomedusae, Phylum Cnidaria. Four species, that is, *Cyanea nozaki* Kishinouye, *Cyanea capillata*, *Cyanea ferruginea* Eschscholtz and *Cyanea purpurea* Kishinouye, have been found at the coast of China, and among them, the *Cyanea nozaki* Kishinouye is predominant, and has the most wide distribution. The *Cyanea nozakii* generally feeds on small zooplanktons, and has developed gonad, high propagation ability, and very quick growth rate. Presently, the annual output of *Cyanea nozakii* in China is up to ten millions tons, thus becoming a new natural marine biological resource.

Marine-derived polysaccharides, proteoglycans, and collagen peptides are very important natural marine food resources, and have significant biological activities. For example, there are many studies and reports about holothurian polysaccharides and seaweed polysaccharides, and it is evidenced that holothurian polysaccharides and seaweed polysaccharides have significant biological activities. Researches and reports about preparation of collagen peptide with *Cyanea nozakii* as raw material through isolation and extraction are still very rare at home and abroad, and there is no reports about isolation and extraction of collagen peptide with immune-enhancing activity so far.

SUMMARY OF THE INVENTION

The present invention is directed to a collagen peptide with immune-enhancing activity from *Cyanea nozakii*, and a preparation method and a use thereof. The present invention is unique, as it adopts a noval natural marine biological resource-*Cyanea nozakii*-as raw material for preparing the collagen peptide, and thus realizing the purpose of development and utilization of *Cyanea nozakii*. Following the present invention, a high-purity collagen peptide product can be obtained with very high yield, which is critical for the comprehensive utilization of the natural marine biological resource *Cyanea nozakii*.

A collagen peptide with immune-enhancing activity from *Cyanea nozakii* is provided, which is a powder characterized by having a white or faint yellow appearance, being odorless, tasted slightly bitter, obtained by isolating and extracting from new finishing products of marine organisms of Family Cyanea including *Cyanea nozaki* Kishinouye, *Cyanea capillata*, *Cyanea ferruginea* Eschscholtz or *Cyanea purpurea* Kishinouyem, or three alum salted products thereof, being non-toxic, having significant immune-enhancing activity, containing 80-90% of proteins and 10-20% of sugars, and having an average molecular weight of 1,000-3,000 Dalton, in which monosaccharides contained therein are mainly glucose, glycine accounts for 16% or above and the sum of proline and hydroxyproline account for 18% or above of amino acid contained therein.

A method for preparing the collagen peptide is provided, which includes:

(1) immersing the *Cyanea nozakii* with water;

(2) performing melting treatment on the immersed *Cyanea nozakii*, and then centrifuging, to obtain a colorless or faint yellow supernatant; and (3) directly drying the supernatant, or homogenizing the supernatant, decolorizing, desalting and then drying, to obtain the collagen peptide as a white or faint yellow powder.

The melting treatment includes melting the *Cyanea nozakii* with water by using a melting agent, to form a liquid.

Specifically, it is found first that the commercially available fresh or three alum salted jellyfish may be used as raw material for preparing collagen peptide after desalting. The contained collagen peptide is stable in water immersing, and will not be degraded due to immersion and thus being extracted into water and lost under the immersion process conditions adopted in the present invention, and the dispersity of the collagen peptide will not be influenced in the subsequent hydrolyzation due to immersion, that is, the commercially available three alum salted jellyfish the new fishing *Cyanea nozakii* have the same processability, and both can be used as raw materials for preparing collagen peptide having high purity and high bioactivity, which underlies the preparation of the collagen peptide having high purity and high bioactivity with *Cyanea nozakii* as raw material.

Secondly, it is found after systematic investigation and comparison of the hydrolyzation conditions such as temperature and pressure and various commonly used melting agents such as sodium hydroxide, hydrochloric acid, and collagenase that, under suitable hydrolyzation conditions, the collagen contained in the *Cyanea nozakii* can be directly hydrolyzed and dispersed into water without being denatured, to obtain a clear and transparent hydrolyzed dispersion substantially free of impurity.

It is found that among the hydrolysis process parameters such as immersion solvent, immersion time, and hydrolyzing agent, the type of the hydrolyzing agent and the hydrolysis temperature are very important for the hydrolysis yield. The effective melting agent includes a common base (for example, a hydroxide or carbonate of sodium, potassium, calcium, and barium, or aqueous ammonia) having a concentration of 0.1-10 molL$^{-1}$; a common acid (for example, an inorganic acid such as hydrochloric acid, phosphoric acid, and sulfuric acid or an organic acid such as formic acid, acetic acid, malic acid, lactic acid, and citric acid) having a concentration of 0.1-10 molL$^{-1}$; or one or more of various proteinases (for example pepsin, trypsin, chymotrypsin, acidic proteinase, basic proteinase, neutral proteinase, papain, bromelain, collagenase, and elastase). The melting treatment is carried out at a pH value of 0.5-14.0, at a temperature of 10-120° C. and an operation pressure of 0.0001-0.5 MPa. When sodium hydroxide is used as the melting agent, the pH value should be in the range of 7.0-14.0, when hydrochloric acid is used as the melting agent, the pH value should be in the range of 0.5-6.8, and when a proteinase is used as melting agent, the pH value should be in the optimum pH range of the selected proteinase. When an acid or a base is used as the melting agent, the melting temperature should be in the range of 10-120° C., and preferably in the range of 0-60° C.; when a proteinase is used as the melting agent, the hydrolyzation should be carried out at an optimum temperature of the proteinase. As for other parameters, the immersion should be carried out in water with a pH value adjusted to be in the range of 2-12, and most preferably in the range of 6.5-6.8, at a temperature in the range of 0-98° C., and most preferably in the range of 0-15° C., till the conductivity of immersion water is lower than 30 $\mu Scm^{-1}$. Centrifugation is carried out for 10-60 min at 0-120° C., and most preferably 0-10° C., at a rotation rate of 4000-12000 rpm, and most preferably 6000-8000 rpm. The liquid may be freeze dried, or spray dried.

It is confirmed through preliminary study that the active collagen peptide from the *Cyanea nozakii* of the present invention has significant immune-enhancing activity, and may be widely used in the fields of foods, health products, skincare cosmetics, and medical products as a novel bioactive material and health food raw material, for preparing medicines, health products, skincare cosmetics having immune-enhancing functions.

BRIEF DESCRIPTION OF THE DRAWINGS

No drawings.

DETAILED DESCRIPTION OF THE INVENTION

The following examples are provided for specifically describing the operation methods of the present invention, but not intended to limit the present invention.

Example 1

After draining water off, 1000 g commercially available three alum salted jellyfish was immersed at room temperature in 2-5 folds of deionized water refreshed every 2-3 hrs, till the content of sodium chloride in the immersion water was lower than 1.5 ppm (negative chloride ion test), and the conductivity of the immersion water was lower than 30 $\mu Scm-1$. The desalted *Cyanea nozakii* after immersion was added with 10 g trypsin having 4000 Units of activity, and isothermically melted for 4-24 hrs at 30-60° C., to obtain a suspension. The suspension was centrifuged (4° C., 8000 rpm, 30 min), and the insoluble residue was discarded, to obtain a collagen peptide solution as a clear and transparent liquid; and then the collagen peptide solution was placed on a rotational evaporator, concentrated to ⅕ of the original volume at 40° C. and 0.001 MPa, and then spray dried (air-in temperature: 185° C.; and air-out temperature: 85° C.), to obtain 20 g of collagen peptide having a purity of above 90% and significant immune-enhancing activity as a solid powder.

The melting may also be carried out at an operation pressure of 0.001 MPa.

Example 2

100 kg fresh *Cyanea nozakii* was immersed at 3-10° C. in 2-5 folds of deionized water refreshed every 2-3 hrs, till the conductivity of the immersion water was lower than 30 $\mu Scm^{-1}$. The desalted *Cyanea nozakii* after immersion was added with 500 g compound enzyme preparation (composed of commercially available trypsin, papain, collagenase, neutral proteinase at a ratio of 1:1:1:1), and isothermically treated for 8-16 hrs at 35-50° C., and then centrifuged at 4° C. and 8000 rpm for 30 min. The insoluble was discarded, to obtain a collagen peptide solution as a clear and transparent liquid; and then the collagen peptide solution was concentrated to ½ of the original volume at 40° C. and 0.001 MPa, and freeze dried, to obtain 1000 g of collagen peptide having a purity of above 95% and significant immune-enhancing activity as a solid powder.

The melting may also be carried out at an operation pressure of 0.1 MPa.

Example 3

The protein content, total sugar content, composition of amino acids, and composition of monosaccharides of a collagen peptide powder sample (for example, prepared following the method in Example 2) were determined. The determination results show that the sample contains 88% of proteins, and 10.5% of sugars, and has an average molecular weight of 1274. The contained monosaccharides are mainly glucose, and the composition of the amino acids contained is as shown in Table 1.

TABLE 1

Composition of amino acids of the test sample

| Amino acid | Content (mg/g) | % |
|---|---|---|
| Aspartic acid | 6.36229 | 8.66 |
| Glutamic acid | 9.64957 | 13.14 |
| Serine | 3.4011 | 4.63 |
| Histidine | 0.1257 | 0.17 |
| Glycine | 12.9557 | 17.64 |
| Threonine | 2.57489 | 3.51 |
| Arginine | 5.43067 | 7.39 |
| Alanine | 4.599921 | 6.26 |
| Tyrosine | 1.02847 | 1.40 |
| Cystine | 0.961188 | 1.31 |
| Valine | 2.43407 | 3.31 |
| Methionine | 0.306633 | 0.42 |
| Phenylalanine | 1.31228 | 1.79 |
| Isoleucine | 1.69354 | 2.31 |
| Leucine | 2.90096 | 3.95 |
| Lysine | 3.48776 | 4.75 |
| Proline | 8.69692 | 11.84 |
| Hydroxyproline | 5.5269 | 7.52 |
| Total amino acid | 73.447851 | |

Example 4

Healthy Kunming mice (female to male 1:1, 4-week old, weight 18-22 g, available from Wuxi Huishan Jiangnan Experimental Animal Farm [Approval No.: SCXK(Su)2002-0006]) were used as experimental animals, to perform acute toxicity test with the resulting collagen peptide powder (for example, prepared following the method in Example 2). The resulting results are shown in Tables 2 and 3.

TABLE 2

Influence of the test sample on the weight of the mice

| | Group | |
|---|---|---|
| Days | Control Group | Test Group |
| 1 d | 22.806 g | 22.667 |
| 2 d | 22.985 g | 23.075 |
| 3 d | 24.300 g | 23.635 |
| 4 d | 24.688 g | 23.766 |
| 5 d | 25.146 g | 24.566 |
| 6 d | 26.084 g | 25.066 |
| 7 d | 26.180 g | 25.966 |

TABLE 3

Results of the acute toxicity test

| Group | Number of Mice | Dose | Weight Growth/ Week | Growth Rate | Mortality |
|---|---|---|---|---|---|
| Control Group | 10 | 0.5 ml/animal | 3.374 g | 14.79% | 0 |
| Test Group | 10 | 7500 mg/kg | 3.299 g | 14.55% | 0 |

It is found through observation that the activities of the mice are decreased in 1 hr after administration, and gradually return to the normal level after 4 hrs. The food intake of the test group in 7 days is gradually increased, and the appetite, spirit, and fur color of the mice are all normal. After 7 days, the animals were sacrificed by dislocating the neck, and lesions and intoxication of major organs such as heart, liver, spleen, lung, and kidney were not observed through autopsy with naked eyes. The animals were daily weighed in the observation period of 7 days, and it was found that the weight of the mice was continuously increased. The research results indicate that in the case of gastric administration of large dose of the test sample, the mortality of the mice and obvious toxicity response do not occur. It is suggested that the collagen peptide has no or little toxicity, with the maximal safety dose being up to 7500 mg/Kg.

Example 5

Healthy Kunming mice (female to male 1:1, 4-week old, weight 18-22 g, available from Wuxi Huishan Jiangnan Experimental Animal Farm [Approval No.: SCXK(Su)2002-0006]) were used as experimental animals, to perform immune-enhancing test with the resulting collagen peptide powder (for example, prepared following the method in Example 2). The resulting results are shown in Tables 4-6.

1 Determination of serum hemolysin of the mice

TABLE 4

Influence of the test sample on serum hemolysin of the mice

| Group | Dose (mg/kg) | Hemolysin Cotent |
|---|---|---|
| Control Group | — | 0.25 ± 0.03 |
| Test Group | 25 | 0.26 ± 0.04 |
|  | 50 | 0.28 ± 0.05 |
|  | 100 | 0.40 ± 0.11* |

Variance analysis, P < 005;
compared with the control group *P < 0.05

Hemolysin (IgM) is a tool for reflecting the state of humoral immune function condition, if more hemolysin is generated after administration, the absorbance is increased in hemolysis of erythrocyte, which suggests that the humoral immune function of an organism is enhanced after administration. It can be known from the results shown in Table 4 that significant difference (P<005) exists between the high-dose group and the control group as shown through comparison, and no significant difference (P>0.05) exists between the low-dose group, medium-dose group, and the control group as shown through comparison, which indicates that the high-dose test sample has obvious effect on the generation of serum hemolysin (IgM), and thus exhibiting good humoral immune-enhancing effect.

2 Determination of delayed-type hypersensitivity (DTH) of the mice

TABLE 5

Influence of the test sample on DTH of the mice

| Group | Dose (mg/kg) | Weight Difference of the Left and the Right Auricles (mg) |
|---|---|---|
| Control Group | — | 3.40 ± 1.01 |
| Test Group | 25 | 6.55 ± 1.62 |
|  | 50 | 11.05 ± 5.35** |
|  | 100 | 4.00 ± 2.12 |

Variance analysis, P < 0.01;
compared with the control group **P < 0.01

DTH is a method for reflecting the state of cell immune function. It can be known from Table 5 that the weight difference of the left and the right auricles of the mice in the test group is slightly increased, as compared with that of the control group, highly significant difference (P<0.01) exists between the medium-dose group and the control group as shown through comparison, and no significant difference (P>0.05) exists between the low-dose group and high-dose group and the control group as shown through comparison, which suggests that the test sample can significantly improve the cellular immune function of the mice in a certain concentration range.

3 Determination of the phagocytic function of phagocyte of the mice

TABLE 6

Influence of test sample on the phagocytic function of phagocyte of the mice

| Group | Dose (mg/kg) | Phagocytic Percentage (%) | Phagocytic Index |
|---|---|---|---|
| Control Group | — | 33.83 ± 1.05 | 2.23 ± 0.17 |
| Test Group | 25 | 2.58 ± 1.16 | 2.25 ± 1.00 |
|  | 50 | 46.15 ± 2.12* | 5.52 ± 0.56** |
|  | 100 | 58.50 ± 2.04* | 6.30 ± 1.06** |

Variance analysis, P < 001;
compared with the control group *P < 0.05;
**P < 001

The phagocytic function of phagocyte is a method for reflecting the state of non-specific immune function. It can be known from Table 6 that significant difference (P<0.05) exists between the phagocytic percentages of the medium-dose group, high-dose group, and the control group as shown through comparison, significant difference (P<0.01) exists between phagocytic indexes of the medium-dose group and high-dose group and the control group as shown through comparison, and no difference (P>0.05) exists between the low-dose group and the control group as shown through comparison, which suggests that a certain dose of test sample can activate the phagocytic activity, and improve the phagocytic function of a mononuclear phagocyte system.

The immune-enhancing experiment results show that a certain dose of test sample can enhance the humoral immune function, the cellular immune function, and the mononuclear phagocyte function of the mouse to some degree.

According to the functional assessment test method, it can be determined that the test sample has the immune-enhancing function, if a positive result is shown in any two of the four following aspects: the cellular immune function, the humoral immune function, the mononuclear phagocyte function, and NK cell activity. In this experiment, positive results are shown in three aspects including the cellular immune function, the humoral immune function, and the mononuclear phagocyte function of the experimental mice, and thus the test sample are determined to have immune-enhancing function.

What is claimed is:

1. A method for preparing extracts comprising collagen peptides from *Cyanea nozakii*, comprising:
   (1) immersing *Cyanea nozakii* into water;
   (2) performing melting treatment on the immersed *Cyanea nozakii* with a melting agent selected from the group consisting of a base, an acid, a proteinase and a mixture thereof, and then centrifuging, to obtain a colorless or faint yellow supernatant; and
   (3) directly drying the supernatant, or homogenizing the supernatant, decolorizing, desalting and then drying, to obtain the extracts comprising collagen peptides as a white or faint yellow powder, wherein the extracts comprise 80-90% of proteins and 10-20% of sugars, wherein an average molecular weight of collagen peptides is 1,000-3,000 dalton, and the extracts are non-toxic with immune-enhancing activity, and wherein the sugar component comprises glucose, and the amino acids contained in the collagen peptides have glycine at least 16% and a sum of proline and hydroxyproline at least 18%.

2. The method for preparing extracts from *Cyanea nozakii* according to claim 1, wherein the *Cyanea nozakii* is immersed in water with a pH value adjusted to be in the range of 2-12 at a temperature in the range of 0-98° C., till the conductivity of the immersion water is lower than 30 $\mu Scm^{-1}$.

3. The method for preparing extracts from *Cyanea nozakii* according to claim 1, wherein the melting treatment comprises melting the *Cyanea nozakii* with water by using the melting agent to form a liquid.

4. The method for preparing extracts from *Cyanea nozakii* according to claim 3, wherein the melting treatment is carried out at a pH value of 0.5-14.0, at a temperature of 10-120° C. and an operation pressure of 0.0001-0.5 MPa.

5. The method for preparing extracts from *Cyanea nozakii* according to claim 1, wherein the base is a hydroxide or carbonate of sodium, potassium, calcium, or barium, or aqueous ammonia, and has a concentration of 0.1-10 $molL^{-1}$; the acid is hydrochloric acid, phosphoric acid, sulfuric acid, formic acid, acetic acid, malic acid, lactic acid or citric acid, and has a concentration of 1-10 $molL^{-1}$; and the proteinase is one or more of pepsin, trypsin, chymotrypsin, an acidic proteinase, a basic proteinase, a neutral proteinase, papain, bromelain, collagenase, and elastase.

6. The method for preparing extracts from *Cyanea nozakii* according to claim 1, wherein the drying is freeze drying or spray drying.

7. The method for preparing extracts from *Cyanea nozakii* according to claim 1, wherein the extracts are isolated from new finishing products of marine organisms of Family Cyanea including *Cyanea nozaki* Kishinouye, *Cyanea capillata*, *Cyanea ferruginea* Eschscholtz or *Cyanea purpurea* Kishinouyem, or three alum salted products thereof.

8. Extracts prepared from *Cyanea nozakii* according to the method of claim 1, wherein the extracts comprise collagen peptides with an average molecular weight being of 1,000-3,000 dalton and immune-enhancing activity.

9. A health product contains the extracts from *Cyanea nozakii* of claim 8.

10. A food, which contains extracts from *Cyanea nozakii* of claim 8.

* * * * *